Figure 1:
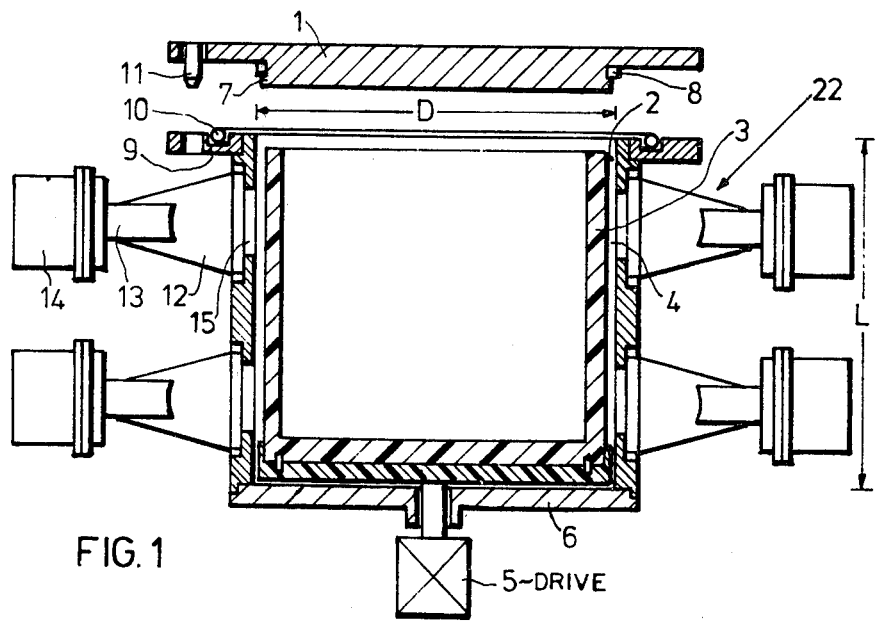

United States Patent [19]

Fitzky et al.

[11] 4,211,970
[45] Jul. 8, 1980

[54] APPARATUS FOR DETERMINING THE WATER CONTENT OF ISOTROPIC MATERIALS

[75] Inventors: Hans G. Fitzky, Odenthal-Hahnenberg; Franz Schmitt, Cologne; Norbert Bollongino, Leichlingen; Helmut Rehrmann, Leverkusen, all of Fed. Rep. of Germany

[73] Assignee: Bayer Aktiengesellschaft, Leverkusen, Fed. Rep. of Germany

[21] Appl. No.: 910,557

[22] Filed: May 30, 1978

[30] Foreign Application Priority Data

Jun. 2, 1977 [DE] Fed. Rep. of Germany ....... 2724959

[51] Int. Cl.² ............................................. G01R 27/04
[52] U.S. Cl. ............................ 324/58.5 C; 324/58.5 A
[58] Field of Search ..................... 324/58.5 C, 58.5 A, 324/58.5 R, 58 C, 58 A

[56] References Cited

U.S. PATENT DOCUMENTS

| | | | |
|---|---|---|---|
| 3,265,967 | 8/1966 | Heald | 324/58.5 A |
| 3,426,247 | 2/1969 | Loyen | 324/58.5 A X |
| 3,430,139 | 2/1969 | Schluter | 324/58.5 A |
| 3,439,266 | 4/1969 | Rogers | 324/58 A |
| 3,482,161 | 12/1969 | Poulter | 324/58.5 A |
| 3,691,454 | 9/1972 | Hrubesh et al. | 324/58.5 C X |
| 3,737,770 | 6/1973 | Masson et al. | 324/58.5 C |
| 3,946,308 | 3/1976 | Miura et al. | 324/58.5 C |
| 4,131,845 | 12/1978 | Pakulis | 324/58.5 A |

Primary Examiner—Rudolph V. Rolinec
Assistant Examiner—Ernest F. Karlsen
Attorney, Agent, or Firm—Sprung, Felfe, Horn, Lynch & Kramer

[57] ABSTRACT

The water content of electrically non-conductive powders, granulates, pastes and fibrous materials may be measured on the basis of microwave absorption. A frequency-modulated microwave oscillator supplies a closed multimode measuring resonator charged with the sample in a transmission arrangement. The sample charged into a container almost completely fills the multimode resonator. The sample container is rotatable about its longitudinal axis. A substantial homogeneity of the field distribution in the sample is thus obtained so that even in the case of variations in the bulk density, accurate measurements are still possible.

14 Claims, 4 Drawing Figures

APPARATUS FOR DETERMINING THE WATER CONTENT OF ISOTROPIC MATERIALS

This invention relates to an apparatus for measuring the water content of electrically non-conductive powders, granulates pastes and other isotropic materials comprising a frequency-modulated oscillator supplying a closed multimode measuring resonator in a transmission arrangement, which multimode measuring resonator is charged with the sample, and a device for measuring the change in quality of the resonator induced by the sample.

It is important to be able to rapidly determine the water content of powders, granulates, pastes and fibrous material for large-scale production of these materials. Examples include pharmaceutical products, synthetic granulates, raw materials for washing agents and finished products, building materials and starting materials for ceramics and agricultural products.

A rapidly operating measuring device is required for monitoring industrial production and processing of these products, the measured results of which may be used, among other things, for controlling the course of operation or for quality control during final inspection.

Instruments for measuring the water content of isotropic materials such as bulk products and pastes, described in the literature are usually designed as free jet devices which are provided for checking continuously moving material and which supply only relatively inaccurate results owing to the varying bulk densities and reflections of the measuring ray or whose technical design is not suitable for rapid and precise routine measurement in operating laboratories (German Offenlegungsschrift No. 2,017,061) and German Offenlegungsschrift No. 2,309,278). Microwave moisture measuring devices for pulverulent or granular products are described in the "GIT-Fachzeitzchrift fur das laboratorium", 1974 volume, pages 869 to 880 and pages 994 to 1000. The change in quality of the resonator owing to the sample is measured. The resonator is supplied with a frequency-modulated microwave oscillator. The frequency deviation is selected sufficiently large for the resonance curve of the resonator to be completely covered both in the empty state, without a sample, and in the full state, with a sample.

Downstream of the transmission resonator is located a microwave detector whose direct-current voltage signal supplies a direct gauge as to the moisture content of the material. However, it has been found when working with such devices that the accuracy of measurement varies considerably. It has been found that the accuracy depends upon the quantity of sample used. It has also been found that even small variations in the bulk density of the product affect the measured result significantly. The latter effect is particularly disturbing when such devices are used as routine measuring devices in the laboratory.

An object of the invention is to improve the known multimode resonator measuring technology for determining the water content of large-volume powder and granulate samples with regard to the accuracy and reproducibility of measurement. In particular, disturbances in the accuracy of measurement owing to local non-homogeneity of sample product such as, for example, variations in particles sizes and bulk density are to be avoided.

In accordance with the invention there is provided an apparatus for measuring the water content of electrically non-conductive powders, granulates, pastes and other isotropic materials, comprising a frequency-modulated microwave oscillator, which supplies a closed multimode measuring resonator said resonator comprising a cylindrical sample contained rotatable about its cylindrical axis and a device for measuring in a transmission arrangement, the change in quality of the said resonator induced by a sample, if the sample loaded into a sample container fills out the multimode resonator almost completely and in that the sample container is rotatable about its cylinder axis and in conjunction with the frequency modulation technique for the modulating of the plurality of excited modes, sufficient homogeneity in the field distribution and in the power-flow is generally obtained allowing a measurement accuracy of ±5% to still be possible, even with local non-homogeneity of the sample product.

The cylindrical multimode resonator is advantageously dimensioned in such a way that $0.5 < D/L < 2$ and $D > 3 \lambda$ is fulfilled. D represents the diameter, L represents the length of the resonator and $\lambda$ the microwavelength. A further improvement with regard to the homogeneous field distribution is obtained by providing low-reflective inlets for the microwaves on from 1 to 4 points on the cylinder wall or on the base at equal intervals in the height and/or in the azimuth at intervals of 90°.

The invention also comprises for integral ray absorption in the entire measuring volume, detectors (microwave rectifiers), which are arranged at from 1 to 4 points on the cylinder wall or on the base at equal intervals in height and/or azimuthal intervals of 90°. These detectors are connected to a summation circuit for displaying the transmission value.

The sample container advantageously consists of a thinwalled removable cylindrical polytetrafluorethylene container filling out the entire inner chamber, which polytetrafluoroethylene container may be displaced in an axial rotation at a rate of more than one rotation per second.

According to a preferred embodiment of the invention the multimode resonator is provided with a detachable covering plate which forms a reproducible and emission-free microwave contact by means for an annular passage filled with polytetrafluorethylene to half the depth of the projection of the internal face of the cover into the resonator and by means of a metal contact-free support of the cover flange on the counter-flange on the cylinder component.

The change in the quality factor of the multimode resonator during introduction of the sample is used for measuring the product-dependent microwave absorption. A differential circuit which forms the difference between the rectified microwave signal at the input to the resonator (reference signal) and the rectified microwave signal (sum) at the resonator output (transmission signal) has proved useful for this purpose. This difference may be displayed digitally.

An advantage of the invention lies as already mentioned, in the increased accuracy of measurement and reproducibility in the case of large-volume powder and granulate samples of differing composition and differing bulk density. The special design of the sample container also allows rapid measurement. The sample product weighed into the container may be introduced directly from the scales into the measuring resonator. The reproducible sample mounting, on the one hand, and the means for homogenising the field, on the other hand, allow the measured value to be detected independently of the position.

With reference to the accompanying drawings

Figure 2:
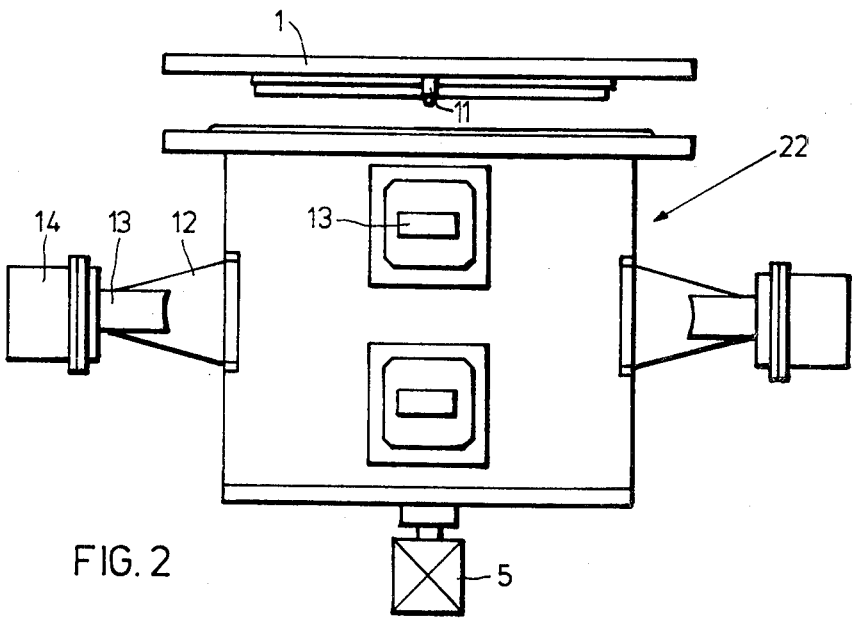
Figure 3:
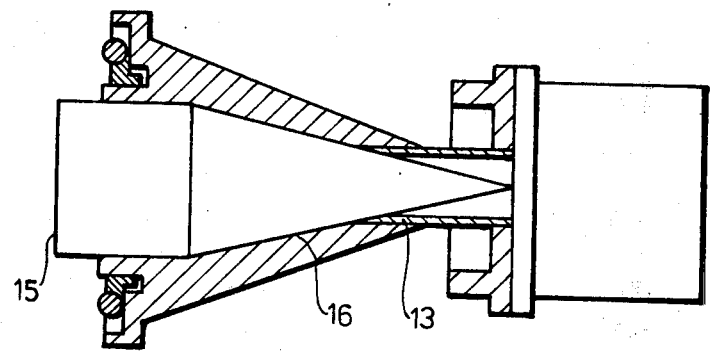
Figure 4:
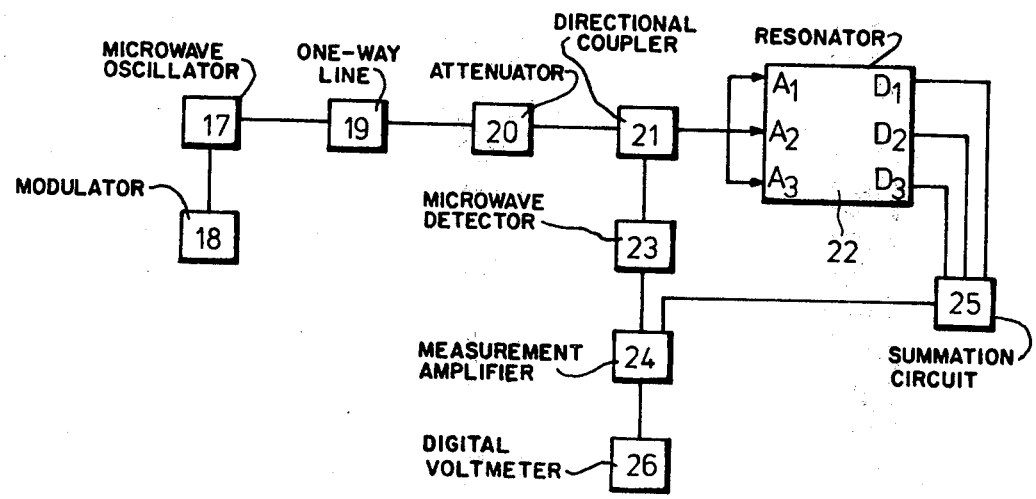

FIG. 1 shows a side view of the measuring resonator,

FIG. 2 also shows a side view in which the measuring resonator is rotated about 90° in relation to FIG. 1, FIG. 3 shows the coupling in and out of the microwaves to/from the resonator, and FIG. 4 shows a block diagram of the entire microwave moisture content measuring device with multimode resonator.

The resonator in FIGS. 1 and 2 comprises a cylindrical hollow chamber 2 which may be closed by a lid 1. A cylindrical sample container 3 which is preferably thin-walled having a wall thickness of from 1 to 3 mm produced from polytetrafluorethylene may be inserted in this hollow chamber. The sample container 3 practically fills the entire resonator chamber so that only a small gap 4 remains between the container wall and the internal wall of the resonator. Interfering resonances are avoided in this way in the area between the container and resonator wall. The sample container 3 is rotatable about its longitudinal axis. A drive 5 for the sample container 3 is located on the base 6 of the resonator. The sample container 3 may additionally be connected to one or more metal vanes which cause additional modulation of the wave fields owing to variable reflection ratios (based on the coupling in and out of the radiation). A rotational frequency of between 1 and 20 Hz is generally sufficient.

With regard to length L and diameter D, the resonator is dimensioned in such a way that $0.5 < D/L < 2$ and $D > 3\lambda$ ($\lambda$ = microwavelength). The smaller the measured wavelength is in relation to the dimensions of the vessel the better is the homogeneousness of the measuring field.

The lid 1 for closing the resonator comprises a metal plate which is thicker in the area of the inner chamber of the resonator. In the closed state, the part 7 of the lid projecting into the resonator chamber forms an annular passage with the internal wall of the resonator, which, annular passage is filled out up to half the depth of the projection with a Teflon ring 8. This polytetrafluorethylene ring 8 and another gasket 10 which lies in a groove 9 located outside the resonator chamber, allow the lid flange to be supported free of metal contact on the counter-flange on the resonator. In this way, the lid 1 forms with the counter-flange on the resonator a reproducible radiation-free microwave contact.

The microwave is simultaneously coupled in at 3 points with the aid of adapters 12. The adapters provide for low-reflective transfer of the microwave energy from rectangular wave-guides 13 into the resonator. The introduction of the microwave on three sides contributes substantially to an improvement in the field homogeneity in the resonator chamber 2. The transmission signal is scanned by means of three detectors 14 (microwave rectifiers or diodes). The three detectors 14 are off-set laterally just like the adapters 12, wherein adapters and detectors face each other (see also FIG. 2). The microwave diodes are located in the rectangular waveguides 13 in the course of the coupling out from the resonator and also the coupling in through circular apertures 15. The microwave is transmitted from the resonator into the rectangular waveguide 13 as in the reverse direction by way of the adapters 12. The wideband low-reflective coupling in and out takes place by means of a Teflon cone 16 which completely fills out the cross-section of the opening 15 and projects with its point into the $H_{10}$ rectangular waveguide 13 (see FIG. 3).

The microwave arrangement for measuring the transmission signal is described with reference to the block diagram FIG. 4. A frequency-modulated microwave oscillator 17 connected to a modulator 18 emits in the covered frequency range a substantially constant power to the subsequent measuring arrangement. Its frequency range is from 3 to 30 GHz. The frequency deviation is regulated between 10 and 10,000 MHz. The modulation frequency may be selected in the range from 1 to Hz to 100 kHz. This selection of the measurement frequency is determined by the position of the peak of the water band, wherein the exact position of the peak is influenced by the temperature and the bonding strength of the water. In this context, reference is to be made to the possibility of minimizing the effect of temperature, by the measurement, by choice, of a frequency which is favourable for a specific temperature interval, for example, the microwave absorption of free water at 9.3 GHz at 10° to 30° C. (absorption value at 10° C. placed at 100) falls from 100 to 68 while it rises from 100 to 113 at 24 GHz. The peak of absorption lies at 9.3 GHz at about 0° C. and at 24 GHz at about 30° C. Generally speaking, higher temperatures displace the peak of absorption to higher frequencies (shorter relaxation period of the water dipole) while a firmer combination of the water dipole, for example in a markedly polar matrix, leads to a reduction in the frequency of the absorption peak. For this reason, the arrangement described herein for measuring relatively high water contents in the order of from 5 to 15% by weight is operated at higher frequencies than, for example, devices which are designed for determining the residual moisture (strong water bonding). A further criterion for the selection of the measurement frequency is that the measurement wavelength should be selected as small as possible in relation to the dimensions of the sample container 3 so as to improve the homogeneity of the measurement field. The radiation emitted by the oscillator 17 is fed via a one-way line 19, an attenuator 20 and a directional coupler 21 to a multimode resonator 22. The intensity $I_0$ at the input A1, A2, A3 of the resonator 22 is measured with a microwave detector 23 whose direct-current voltage signal is fed to a measurement amplifier 24. As already mentioned in the description of FIG. 1, the feeding of the microwave into the measurement resonator 22 takes place at several points A1, A2, A3 offset in height and in azimuth. The same microwave power is fed to the three coupling-in points A1,A2,A3 with the lid of a power divider. By feeding in at various points, it is possible to excite very many natural oscillations of the multimode resonator and for a substantially homogeneous distribution of intensity to be regulated in the resonator chamber.

Similarly, identically distributed measurement detectors D1, D2, D3 (microwave diodes 14, see FIG. 1) are provided for detecting the microwave absorption in all volume elements of the resonator, the direct-current output signals of which measurement detectors are added in a summation circuit 25. The summation signal is fed to the other input of the measurement amplifier 24 which forms the difference between this signal and the reference signal $I_0$. This difference represents the unknown quantity for the water content and is displayed directly by a digital voltmeter 26.

The sample container 3 need not be completely filled with the sample. However, it is beneficial when measuring this material to weigh in constant amounts. The motor 5 is regulated in such a way that the sample container 3 rotates slowly at a frequency of from 1 to 5 rotations per second. With materials of good homogeneity the rotating container may be dispensed with and the product may be charged directly into the metallic hollow chamber 2. The accuracy of measurement in this arrangement is at worst ±5% of the measured value, of considerable importance for the reproducibility of measurement is the contact-free and radiation-tight seal of the measuring resonator 22 by the special lid design 1.

What we claim is:

1. An apparatus for measuring the water content of electrically non-conductive powders, granulates, pastes and other isotropic materials, comprising a frequency-modulated microwave oscillator for supplying a frequency modulated microwave a closed cylindrical multimode measuring resonator receptive of the frequency modulated microwave, and dimensioned according to $0.5 < D/L < 2$ and $D > 3\lambda$ where D is the diameter and L is the length of the resonator and $\lambda$ is the microwave length to thereby be excitable in a plurality of modes a cylindrical sample container rotatably mountable about its cylindrical axis within the resonator and filling the volume thereof such that any annular gap therebetween is insufficient to produce interfering resonances therein and means for detecting the microwave transmitted through the resonator.

2. An apparatus according to claim 1, further comprising means for regulating the frequency deviation of the microwave oscillator exciting the resonator such that a maximum number of natural resonances is excited in order that a substantially homogeneous distribution of energy density is obtained.

3. An apparatus according to claim 1, wherein the frequency of the microwave oscillator lies between 2 and 30 GHz.

4. An apparatus according to claim 3, wherein the frequency deviation lies between 10 and 10,000 MHz.

5. An apparatus according to claim 4 wherein the modulation frequency lies between 1Hz and 100 KHz.

6. An apparatus according to claim 1, wherein the detecting means comprises microwave detectors arranged for measuring the integral radiation absorption in the entire measurement volume, at 1 to 4 points on one of the cylindrical wall and the base of the resonator at equal distances in at least one of height and azimuth at intervals of 90 degrees, a summation circuit connected to the microwave detectors and means for displaying the transmission value.

7. An apparatus according to claim 1, wherein for exciting homogeneous internal field, the resonator comprises low-reflective inputs for the microwaves at from 1 to 4 points on one of the cylinder wall and the base at equal intervals in at least one of height and azimuth at intervals of 90° degrees.

8. An apparatus according to claim 6, wherein the detecting means comprises a differential circuit which forms the difference between a rectified microwave signal at the input to the measurement resonator and a rectified microwave signal at the resonator output after the summation achieved by the summation circuit.

9. An apparatus according to claim 8, wherein the difference is displayed digitally.

10. An apparatus according to claim 1, wherein the container is a thin-walled removable cylindrical polytetrafluoroethylene container and further comprising means for rotating the container at a rotational speed of more than 1 rotation per second.

11. An apparatus according to claim 10, wherein the wall thickness of the container is from 1 to 3 mm.

12. An apparatus according to claim 1, wherein the multimode resonator is provided with a removable cover plate comprising a flange having a diameter configured to define an annular passage with respect to the inner surface of the resonator, the annular passage filled to half way up with polytetrafluoroethylene and means for effecting a metal contact-free support of the flange disposed on a counter flange on the cylindrical part of the resonator.

13. A method for measuring the water content of electrically non-conductive powders, granulates, pastes and other isotropic materials comprising: providing a closed cylindrical multimode measuring microwave resonator dimensioned according to $0.5 < D/L < 2$ and $D \leq 3\lambda$, where D is the diameter and L is the length of the resonator and $\lambda$ is the microwave length; inserting a cylindrical sample container within the resonator to fill same such that any annular gap therebetween is insufficient to produce interfering resonances therein; supplying a frequency modulated microwave to the resonator to excite the resonator in a plurality of modes; rotating the sample container about its cylindrical axis; and detecting the microwave transmitted through the resonator.

14. A method as claimed in claim 13 further comprising measuring substantially the same quantity of sample into the container in unsuccessive tests in order to obtain comparable measurements.

* * * * *

UNITED STATES PATENT AND TRADEMARK OFFICE
CERTIFICATE OF CORRECTION

PATENT NO. : 4,211,970
DATED : July 8, 1980
INVENTOR(S) : Hans Georg Fitzky, et al It is certified that error appears in the above-identified patent and that said Letters Patent are hereby corrected as shown below:

Col. 1, line 39, "fur" should be --für--

Col. 4, line 44, "The" first occurrence, should start new paragraph.

Col. 4, line 56, "osciallations" should be --oscillations--.

Col. 6, line 38, "$\leq$" should be -- $>$ --.

Signed and Sealed this

Fourth Day of November 1980

[SEAL]

Attest:

SIDNEY A. DIAMOND

Attesting Officer

Commissioner of Patents and Trademarks